(12) United States Patent
Petit

(10) Patent No.: US 11,690,962 B2
(45) Date of Patent: Jul. 4, 2023

(54) FLUID OR POWDERY PRODUCT DISPENSING DEVICE

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 721 days.

(21) Appl. No.: 16/614,822

(22) PCT Filed: Jun. 4, 2018

(86) PCT No.: PCT/FR2018/051281
§ 371 (c)(1),
(2) Date: Nov. 19, 2019

(87) PCT Pub. No.: WO2018/224762
PCT Pub. Date: Dec. 13, 2018

(65) Prior Publication Data
US 2020/0197630 A1    Jun. 25, 2020

(30) Foreign Application Priority Data

Jun. 6, 2017 (FR) ...................................... 1754977

(51) Int. Cl.
*A61M 11/00*  (2006.01)
*A61M 16/14*  (2006.01)
*B05B 11/06*  (2006.01)

(52) U.S. Cl.
CPC .......... *A61M 11/007* (2014.02); *A61M 16/14* (2013.01); *B05B 11/062* (2013.01);
(Continued)

(58) Field of Classification Search
CPC .. A61M 11/00; A61M 11/006; A61M 11/007; A61M 11/008; A61M 11/02;
(Continued)

(56) References Cited

U.S. PATENT DOCUMENTS

| | | | |
|---|---|---|---|
| 5,284,132 A * | 2/1994 | Geier | .................... B05B 11/007 |
| | | | 128/200.22 |
| 5,307,953 A * | 5/1994 | Regan | .................. A61M 11/007 |
| | | | 604/203 |

(Continued)

FOREIGN PATENT DOCUMENTS

| WO | 99/34853 A1 | 7/1999 |
|---|---|---|
| WO | 99/46055 A1 | 9/1999 |

(Continued)

OTHER PUBLICATIONS

International Preliminary Report on Patentability with Written Opinion dated Dec. 10, 2019 from the International Bureau in International Application No. PCT/FR2018/051281.

(Continued)

*Primary Examiner* — Colin W Stuart
(74) *Attorney, Agent, or Firm* — Sughrue Mion, PLLC

(57) ABSTRACT

A dispenser device for fluid or powder, including an air expeller (20) and a reservoir (30). The reservoir (30) has an air inlet (31) connected to the air expeller (20) and a composition outlet (32) connected to a dispenser opening (10), and is removably mounted on the air expeller. After actuation, the empty reservoir can be removed from the air expeller and replaced with a new reservoir. The air inlet (31) is closed by a first closure element (40) and the composition outlet (32) is closed by a second closure element (50). A mechanical opening system (61, 62) co-operates with the first and second closure elements to expel each closure element from the closed position. The mechanical opening system has a first rod (61) secured to the air expeller (20), (Continued)

and a second rod (62) secured to the dispenser head (1), co-operating with a closure element during actuation.

18 Claims, 2 Drawing Sheets

(52) U.S. Cl.
CPC ... *A61M 2202/04* (2013.01); *A61M 2202/064* (2013.01); *A61M 2205/073* (2013.01)

(58) Field of Classification Search
CPC .............. A61M 15/00; A61M 15/0028; A61M 15/0043; A61M 15/08; A61M 2202/04; A61M 2202/064; A61M 2205/07; A61M 2205/071; A61M 2205/073
See application file for complete search history.

(56) References Cited

U.S. PATENT DOCUMENTS

| | | | | |
|---|---|---|---|---|
| 5,893,484 | A * | 4/1999 | Fuchs | B05B 11/3094 222/321.6 |
| 5,899,202 | A * | 5/1999 | Ohki | A61M 15/0028 128/203.22 |
| 6,055,979 | A * | 5/2000 | Fuchs | A61M 15/0065 222/211 |
| 6,398,074 | B1 * | 6/2002 | Bruna | A61M 15/0028 222/386 |
| 6,425,499 | B1 * | 7/2002 | Guiffray | A61M 11/007 604/91 |
| 6,877,672 | B2 * | 4/2005 | Stihl | A61M 11/02 239/8 |
| 2002/0092524 | A1 * | 7/2002 | Lockhart | A61M 11/008 128/203.21 |
| 2004/0050885 | A1 * | 3/2004 | Stradella | A61M 11/02 222/633 |
| 2004/0195276 | A1 * | 10/2004 | Fuchs | B05B 11/0083 222/386 |

FOREIGN PATENT DOCUMENTS

| | | |
|---|---|---|
| WO | 02/45866 A1 | 6/2002 |
| WO | 2015/001269 A1 | 1/2015 |
| WO | 2015/001281 A1 | 1/2015 |

OTHER PUBLICATIONS

International Search Report for PCT/FR2018/051281, dated Aug. 22, 2018.

* cited by examiner

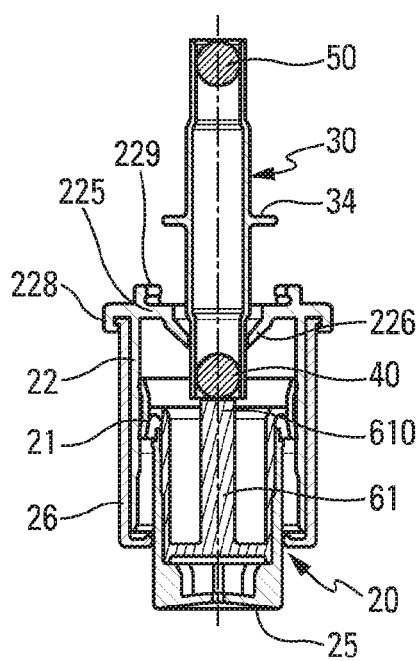
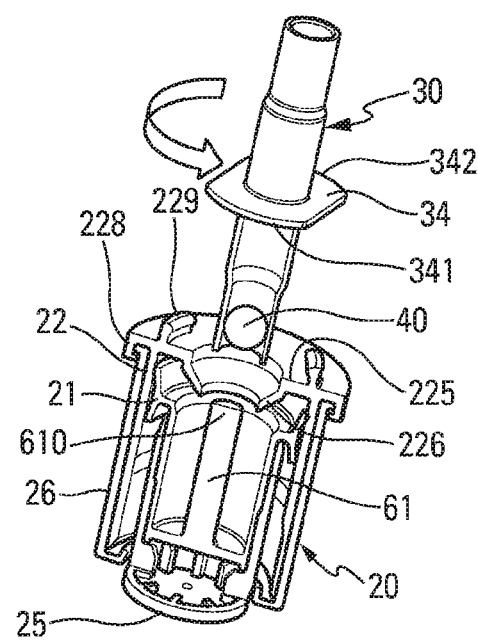
Fig. 10
Fig. 11
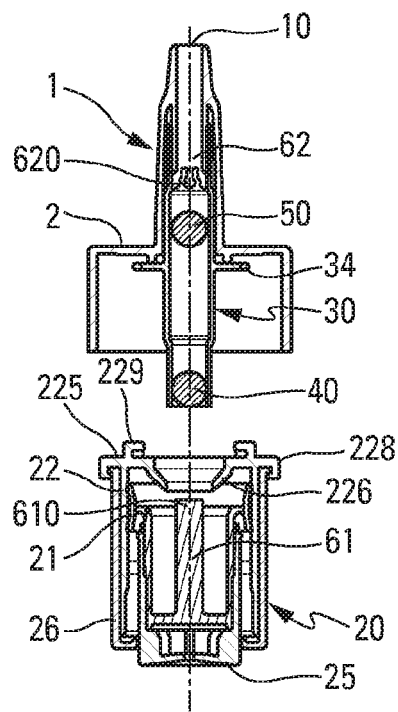
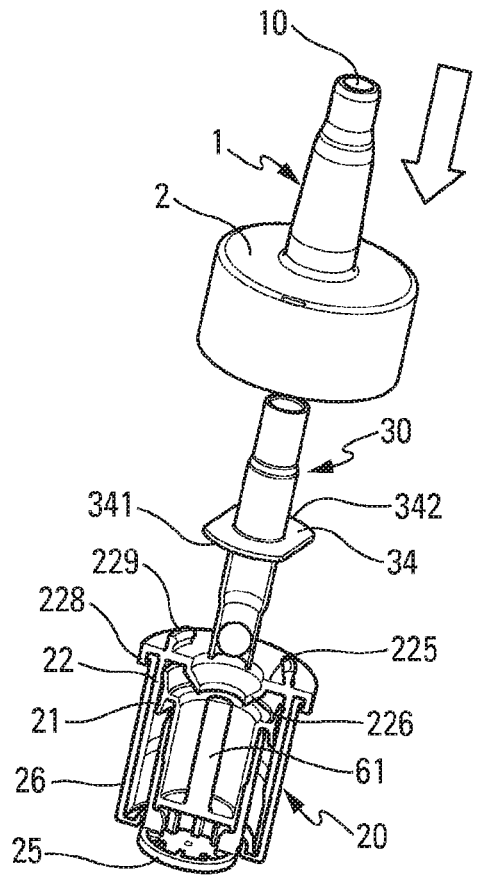
Fig. 12
Fig. 13

FLUID OR POWDERY PRODUCT DISPENSING DEVICE

This application is a National Stage of International Application No. PCT/FR2018/051281 filed Jun. 4, 2018, claiming priority based on French Patent Application No. 1754977 filed Jun. 6, 2017.

The present invention relates to a dispenser device for dispensing a fluid or powder composition, and more particularly it relates to a device for dispensing a dose of a composition, in particular powder, contained in a reservoir, by means of a flow of air under pressure.

Document WO 99/46055 discloses such a device in which a spherical closure element, which closes the outlet of the reservoir, is expelled by the flow of air created by an air expeller. In order to use a dispenser device more particularly for dispensing powder, the air pressure necessary for actuating the device must be sufficiently high to guarantee that the dose is dispensed completely, and that it is broken up, if that is necessary. In the above-mentioned device, the air pressure necessary to actuate the device is determined by the resistance opposed by the ball in order to be expelled. That resistance is relatively difficult to control and to predetermine since it depends on the friction between the ball and its cylindrical seat in which it is engaged for the purpose of closing said reservoir in sealed manner. Consequently, it may be necessary to minimize the interference between the sphere and its cylindrical seat, and obviously that might spoil the effectiveness of the closure. Furthermore, it may be necessary to minimize the depth and the positioning of the sphere in its seat so as to make it easier to expel. It may also be necessary to provide air pressure that is relatively high, which is not always easy to achieve by means of a pump system or of a bellows system, in particular when the air expellers are actuated manually by the patient. Furthermore, dispensing, i.e. expelling the ball from its seat, may take place at different positions along the stroke of the pump or of the bellows of the air expeller, such that the precise moment of dispensing the composition cannot always be predetermined in exact manner. Finally, there is a limit on the materials that can be chosen for the sphere and for its seat.

Document WO 02/45866 describes a device in which a closure ball is expelled mechanically by a rod that is secured to an air expeller. That device is not reusable, and the entire device must be thrown away after it has been used. In particular, for ecological and economic reasons, it may be desirable to have a reusable device in which the reservoir is changed after each actuation, but not the air expeller.

Documents WO 2015/001269 and WO 2015/001281 describe devices similar to the device in document WO 02/45866, in which the air expeller of the device can be reused with a plurality of powder reservoirs. Those devices also present drawbacks. Thus, they enable the air expeller to be reused, but not the dispenser head which is thrown away with the reservoir after each use. Furthermore, those devices require a movable part that is connected to the reservoir via breakable bridges, which makes the device difficult to manufacture. Furthermore, during actuation, a sound is generated when the breakable bridges are broken, which can mislead the user. In addition, the devices in documents WO 2015/001269, WO 2015/001281, and WO 02/45866 include a rod that passes through the reservoir, thereby limiting the working volume of said reservoir, and making the reservoir more difficult to fill.

An object of the present invention is to provide a fluid or powder dispenser device that does not have the above-mentioned drawbacks.

In particular, an object of the present invention is to provide such a fluid or powder dispenser device that can be re-used a plurality of times with a plurality of different reservoirs.

An object of the present invention is also to provide a fluid or powder dispenser device that is simple and inexpensive to manufacture, to assemble, to fill, and to use.

The present invention thus provides a dispenser device for dispensing a fluid or powder composition, the dispenser device including a dispenser head provided with a dispenser opening, an air expeller for generating a flow of air while the device is being actuated, and at least one reservoir that contains a single dose of composition, said reservoir including an air inlet that is connected to said air expeller, and a composition outlet that is connected to said dispenser opening, said reservoir being mounted in removable manner on said air expeller such that, after the device has been actuated, the empty reservoir can be removed from said air expeller and replaced with a new full reservoir, said air expeller being adapted to return to its rest position so as to make a new actuation possible with said new full reservoir, said air inlet being closed by a first closure element and said composition outlet being closed by a second closure element, said device including a mechanical opening system that co-operates with said first and second closure elements so as to expel each closure element mechanically from its respective closed position while the device is being actuated, said mechanical opening system comprising a first rod that is secured to said air expeller, and a second rod that is secured to said dispenser head, each of said first and second rods co-operating with a respective closure element during actuation, so as to expel it mechanically from its closed position.

Advantageously, said reservoir is symmetrical and the two closure elements are identical.

Advantageously, said reservoir is made as a single piece, in particular by molding.

In a variant, said reservoir is made as two advantageous identical portions, in particular by molding, which portions are fastened together, in particular by welding or by adhesive bonding.

Advantageously, said reservoir comprises a cylindrical main body that is terminated at its axial ends by said air inlet and by said composition outlet.

Advantageously, said air inlet and said composition outlet are formed by cylindrical portions of diameter that is small relative to said main body, thereby enabling them to co-operate in sealed manner with said two closure elements that are forced-fitted therein.

Advantageously, after actuation, said two closure elements are arranged inside said reservoir.

Advantageously, the outside of said reservoir includes a radial flange that extends radially outwards, preferably from approximately the middle of said reservoir, so as to fasten said reservoir on said air expeller.

Advantageously, said radial flange is not circular, but of shape that is approximately rectangular, having a radial extent in a first direction that is greater than its radial extent in a second direction perpendicular to said first direction.

Advantageously, said first closure element and/or said second closure element is/are made as a ball.

Advantageously, said air expeller includes a piston that slides in an air chamber between a rest position and a dispensing position, said piston, when in its rest position, co-operating in non-airtight manner with said air chamber, in such a manner that said air chamber is in communication with the atmosphere in the rest position.

Advantageously, said air chamber comprises a cylindrical body that includes a radial flange at its top axial edge.

Advantageously, on its top surface, said radial flange includes fastener means for fastening said reservoir.

Advantageously, said fastener means comprise projections that form diametrically-opposite shoulders that are adapted to receive said radial flange of said reservoir and to hold it in position axially.

Advantageously, said air expeller is returned manually into its rest position while replacing an empty reservoir with a full reservoir.

These characteristics and advantages and others appear more clearly from the following detailed description, given by way of non-limiting example, and with reference to the accompanying drawings, in which:

FIG. 10 is a section view of a detail of a first assembly variant for assembling a new reservoir in the device;

FIG. 11 is a perspective view of the FIG. 10 first assembly variant;

FIG. 12 is a view similar to the view in FIG. 10, showing a second assembly variant; and FIG. 13 is a perspective view of the FIG. 12 second assembly variant.

Figure 1:
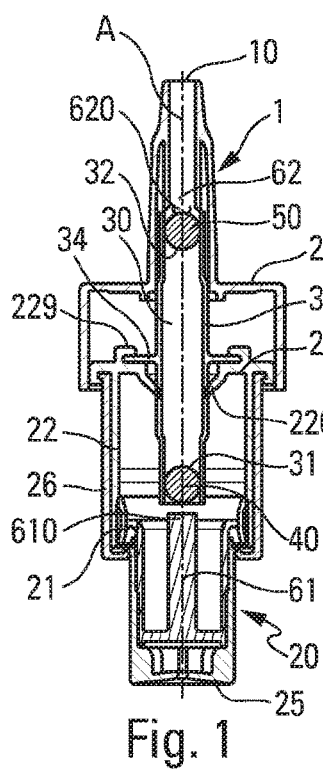
FIG. 1 is a diagrammatic section view of a fluid or powder dispenser device in an advantageous embodiment, in its rest position.

It is understood that throughout the description, the terms "top", "bottom", "upwards", and "downwards" refer to the upright position of the device shown in particular in FIG. 1. The terms "axial" and "radial" refer to the longitudinal central axis A of the device, shown in particular in FIG. 1.

The device includes a reservoir 30 containing a dose of composition to be dispensed, said reservoir 30 including an air inlet 31 and a composition outlet 32. The air inlet 31 of the reservoir is connected to an air expeller 20, and the composition outlet 32 of the reservoir is connected to a dispenser opening 10 of the device. The air inlet 31 is closed by a first closure element 40, in particular a ball, that is force fitted in said air inlet 31. The composition outlet 32 is closed by a second closure element 50, in particular a ball, that is force fitted in said composition outlet 32. Before the device is actuated, the dose of fluid to be dispensed is thus held in said reservoir 30 between said two closure elements 40, 50. The two closure elements 40, 50 preferably guarantee the sealing of the composition contained in the reservoir.

Advantageously, as can be seen in FIGS. 6 to 9, the reservoir 30 is symmetrical, and the two closure elements 40, 50 are identical, such that the reservoir may be used in either of its axial orientations.

Figure 8:
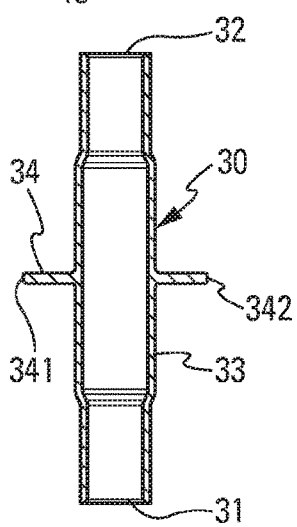
FIGS. 8 and 9 are views of a detail of the reservoir, showing two manufacturing variants of said reservoir.
Figure 9:
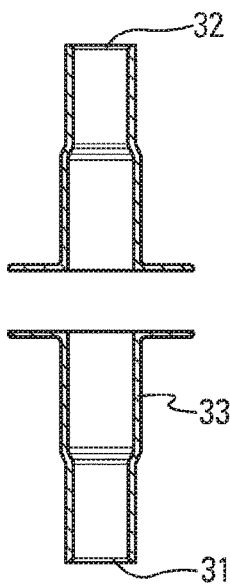

The reservoir 30 may be made, in particular by molding, as a single piece, as shown in FIG. 8. In a variant, it may be made out of two pieces that are advantageously identical, and that are then fastened together, e.g. welded, in particular by ultrasound or by laser, or adhesively-bonded.

Figure 6:
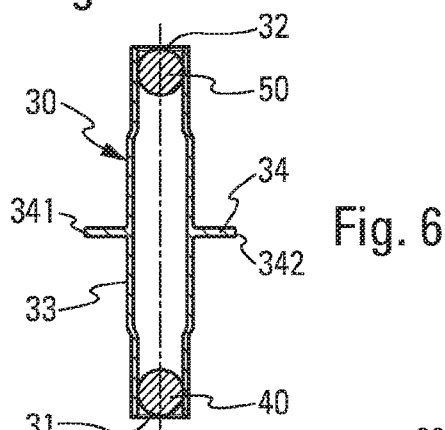
FIGS. 6 and 7 are views of a detail of the reservoir, respectively before and after the device has been actuated.
Figure 7:
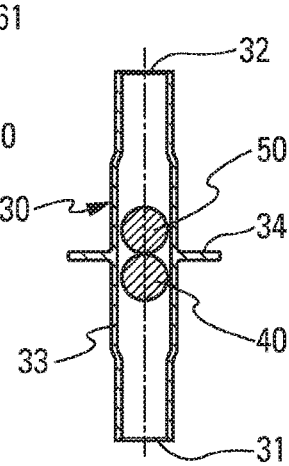

The reservoir 30 advantageously comprises a cylindrical main body 33 that is terminated at its axial ends by said air inlet 31 and said composition outlet 32. Preferably, the air inlet 31 and the composition outlet 32 are formed by cylindrical portions of diameter that is small relative to said main body 33, enabling them to co-operate in sealed manner with the two closure elements 40, 50 that are forced-fitted therein, as shown in FIG. 6. During actuation, the two closure elements 40, 50 are moved inwards inside the reservoir 30, as shown in FIG. 7. The greater diameter of said main body 33 thus makes it possible for a flow of air to enter, and for the composition to be expelled by means of said flow of air, despite the presence of the two closure elements 40, 50. In this embodiment, it is particularly advantageous for the two closure elements 40, 50 to be made as balls, so as to prevent any composition from being retained unintentionally in the reservoir during expulsion.

The outside of the reservoir 30 includes a radial flange 34 that extends radially outwards, preferably from approximately the middle of said reservoir 30, so as to fasten said reservoir 30 on an air expeller 20 as described above. As shown in particular in FIGS. 11 and 13, the radial flange 34 is not circular, but of shape that is approximately rectangular, having a radial extent in a first direction that is greater than its radial extent in a second direction perpendicular to said first direction. Advantageously, the radial end edges 341, 342 in said first direction are rounded. The radial flange 34 serves to fasten the reservoir 30 in removable manner on an air expeller, as described more fully below.

The device includes an air expeller 20 that is actuated manually by the user, and that is adapted to create a flow of air that passes through the reservoir 30 so as to deliver the composition that it contains towards the dispenser outlet 10.

The reservoir 30 is secured, in particular force fitted, in a dispenser head 1 that includes the dispenser opening 10.

The device includes a mechanical opening system 61, 62 that is adapted to co-operate with said first and second closure elements 40 and 50, so as to expel them mechanically from their closed positions while the device is being actuated. In the invention, the mechanical opening system comprises a first rod 61 that is secured to the air expeller 20, and a second rod 62 that is secured to the dispenser head 1. During actuation, each of the rods 61, 62 co-operates with a respective closure element 40, 50, so as to expel it mechanically from its closed position.

The first and second closure elements 40, 50 are preferably spherical, e.g. balls as described above, but they could be non-spherical, e.g. egg-shaped.

The air expeller shown in FIG. 1 includes a piston 21 that slides in an air chamber 22, the piston 21 being actuated manually by the user. Advantageously, such actuation is performed by means of a pusher element 25 that is assembled on said piston 21.

The piston 21 is secured to the first rod 61, advantageously being formed integrally therewith.

The air chamber 22 advantageously comprises a cylindrical body that includes a radial flange 225 at its top axial edge. The radial flange 225 firstly extends radially inwards from said cylindrical body, where it includes an axial extension 226 that extends axially downwards. The purpose of the axial extension 226 is to co-operate, advantageously in substantially airtight manner, with the outer surface of the reservoir 30, when the device is assembled. The radial flange 225 secondly extends radially outwards from said cylindrical body, where it includes fastener means 228 for fastening to an outer body 26 that is assembled around said air chamber 22.

On its top surface, said radial flange 225 includes fastener means 229 for fastening said reservoir 30. The fastener means 229 advantageously comprise projections that form diametrically-opposite shoulders that are adapted to receive the radial flange 34 of said reservoir 30 and to hold it axially in position. The reservoir 30 is thus fastened on the air expeller 20 by a bayonet type fastening, with the radial flange 34 of the reservoir 30 being positioned on the radial flange 225 of the air chamber 22, and with the reservoir then being turned, typically through about 90°, so as to trap said radial flange 34 under the projections 229.

In its rest position, as can be seen in FIG. 1, the air expeller 20 is advantageously open to the atmosphere.

Figure 2:
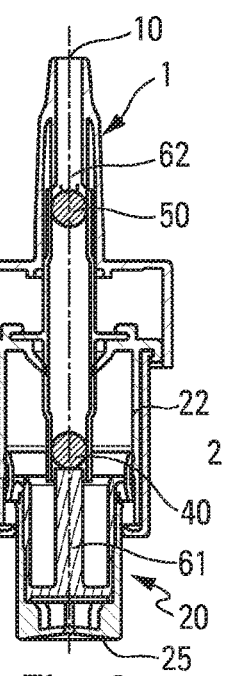
FIGS. 2 to 5 are views similar to the view in FIG. 1, showing various stages of actuation.

Actuation of the device is shown by way of example in FIGS. 2 to 5. Thus, when it is desired to actuate the device, the user firstly places fingers on a finger rest 2 of the dispenser head 1, and secondly a thumb on the pusher element 25, and exerts an actuation force that moves the first rod 61 and the piston 21 towards the dispensing position. At the beginning of actuation, as can be seen in FIG. 2, the piston 21 of the air expeller co-operates in airtight manner with the air chamber 22, such that the air contained in said air chamber 22 is compressed progressively during actuation.

In the FIG. 2 position, the top axial end 610 of the first rod 61 comes into contact with the first closure element 40, and the bottom axial end 620 of the second rod 62 comes into contact with the second closure element 50.

Figure 3:
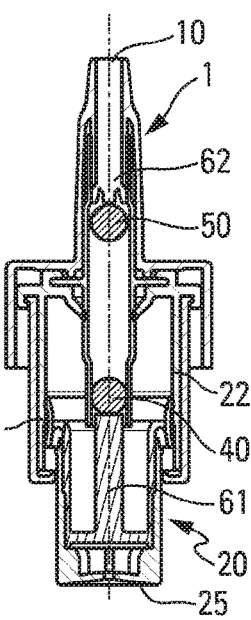

Continuing the actuation initially moves said second closure element 50 downwards, as can be seen in FIGS. 2 and 3. Specifically, since the first rod 61 is secured to the piston 21 of the air expeller, it encounters stronger resistance than the second rod 62.

Actuation thus causes the air contained in the air chamber 22 to be compressed, the composition outlet 32 to open by expelling the second closure element 50 from its closed position, and the air inlet 31 to open by expelling the first closure element 40 from its closed position.

Figure 4:
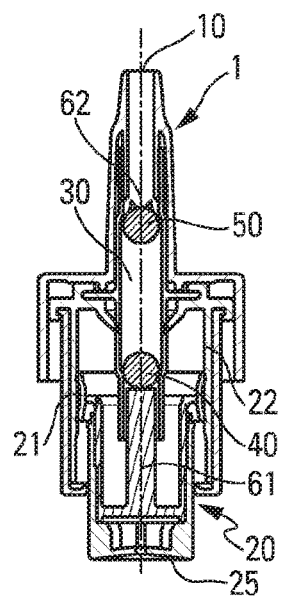

As can be seen in FIGS. 3 and 4, said first closure element 40 is thrust axially upwards into the reservoir 30, and thus away from its closed position sealing the air inlet. At that moment, the compressed air in the air chamber 22 can thus penetrate into the reservoir 30.

Figure 5:
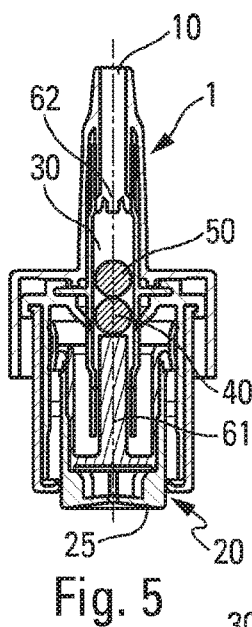

A complete actuation stroke thus expels the entire dose of composition contained in the reservoir 30 by means of a flow of compressed air created by the air expeller 20, as can be seen in FIG. 5.

The present invention relates to a refillable device.

Thus, after actuation, the user can remove the dispenser head 1 from the empty reservoir 30, and can separate said reservoir 30 from the air expeller 20 by turning it through one-fourth of a turn. After the empty reservoir has been removed, as shown in FIG. 10, a new full reservoir 30 can be assembled on the air expeller 20.

FIGS. 10 and 11 show a first variant in which the full reservoir 30 is initially assembled on the air expeller by being moved downwards axially in translation, and then by being turned through one-fourth of a turn as described above, after which the dispenser head 1 is assembled around said assembly formed by the air expeller 20 and the reservoir 30. When the user inserts the reservoir 30 into the air expeller 20, the first rod 61 is pushed downwards, thereby causing the piston 21 to slide back towards its rest position. To do this, the resistance to the piston 21 returning is less than the resistance necessary for moving said first closure element 40 out from its closed position. At the end of axial insertion, the reservoir 30 is turned through one-fourth of a turn, so that the radial flange 34 of the reservoir 30 comes to co-operate with the fastener means. The device is thus ready for a new actuation cycle.

FIGS. 12 and 13 show a second variant in which the dispenser head 1 is initially assembled around the full reservoir 30, and then the assembly formed by said dispenser head 1 and by said full reservoir 30 is assembled on the air expeller 20 by being moved downwards axially in translation, and then by being turned through one-fourth of a turn as described above.

Although intended mainly for dispensing a powder composition, the present invention also applies to dispensing liquids.

The present invention is described above with reference to several embodiments, but naturally any modification could be applied thereto by a person skilled in the art, without going beyond the ambit of the present invention, as defined by the accompanying claims.

The invention claimed is:

1. A dispenser device for dispensing a fluid or powder composition, the dispenser device including a dispenser head provided with a dispenser opening, an air expeller for generating a flow of air while the device is being actuated, and at least one reservoir that contains a single dose of composition, said at least one reservoir including an air inlet that is connected to said air expeller, and a composition outlet that is connected to said dispenser opening, said at least one reservoir being mounted in removable manner on said air expeller such that, after the device has been actuated, the empty reservoir can be removed from said air expeller and replaced with a new full reservoir, said air expeller being adapted to return to its rest position so as to make a new actuation possible with said new full reservoir, said air inlet being closed by a first closure element and said composition outlet being closed by a second closure element, said device including a mechanical opening system that co-operates with said first and second closure elements so as to expel each closure element mechanically from its respective closed position while the device is being actuated, the device being characterized in that said mechanical opening system comprises a first rod that is secured to said air expeller, and a second rod that is secured to said dispenser head, each of said first and second rods co-operating with a respective closure element during actuation, so as to expel it mechanically from its closed position.

2. The device according to claim 1, wherein said at least one reservoir is symmetrical and the two closure elements are identical.

3. The device according to claim 1, wherein said at least one reservoir is made as a single piece.

4. The device according to claim 1, wherein said at least one reservoir is made as two identical portions, which portions are fastened together.

5. The device according to claim 1, wherein said at least one reservoir comprises a cylindrical main body that is terminated at its axial ends by said air inlet and by said composition outlet.

6. The device according to claim 5, wherein said air inlet and said composition outlet are formed by cylindrical portions of diameter that is small relative to said main body, thereby enabling them to co-operate in sealed manner with said two closure elements that are force-fitted therein.

7. The device according to claim 1, wherein, after actuation, said two closure elements are arranged inside said at least one reservoir.

8. The device according to claim 1, wherein an outside of said at least one reservoir includes a radial flange that extends radially outwards so as to fasten said at least one reservoir on said air expeller.

9. The device according to claim 8, wherein said radial flange is not circular, but of shape that is approximately rectangular, having a top radial extent in a first direction that is greater than its radial extent in a second direction perpendicular to said first direction.

10. The device according to claim 1, wherein said first closure element and/or said second closure element is/are made as a ball.

11. The device according to claim 1, wherein said air expeller includes a piston that slides in an air chamber between a rest position and a dispensing position, said piston, when in its rest position, co-operating in non-airtight manner with said air chamber, in such a manner that said air chamber is in communication with the atmosphere in the rest position.

12. The device according to claim 11, wherein said air chamber comprises a cylindrical body that includes a radial flange at its top axial edge.

13. The device according to claim 12, wherein, on its top surface, said radial flange includes fastener means for fastening said at least one reservoir.

14. The device according to claim 13, wherein said fastener means comprise projections that form diametrically-opposite shoulders that are adapted to receive a radial flange of said at least one reservoir and to hold it in position axially.

15. The device according to claim 1, wherein said air expeller is returned manually into its rest position while replacing an empty reservoir with a full reservoir.

16. The device according to claim 1, wherein said at least one reservoir is made as a single piece by molding.

17. The device according to claim 1, wherein said at least one reservoir is made as two identical portions by molding, wherein said two identical portions are fastened together by welding or by adhesive bonding.

18. The device according to claim 1, wherein an outside of said at least one reservoir includes a radial flange that extends radially outwards from a middle of said at least one reservoir, so as to fasten said at least one reservoir on said air expeller.

* * * * *